United States Patent
Wang (10) Patent No.: US 9,582,646 B2
(45) Date of Patent: Feb. 28, 2017

(54) CONNECTED PATIENT MONITORING SYSTEM AND METHOD TO PROVIDE PATIENT-CENTRIC INTELLIGENT MONITORING SERVICES

(71) Applicant: KONINKLIJKE PHILIPS N.V., Eindhoven (NL)

(72) Inventor: Dong Wang, Scarsdale, NY (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/419,248

(22) PCT Filed: Aug. 5, 2013

(86) PCT No.: PCT/IB2013/056401
§ 371 (c)(1),
(2) Date: Feb. 3, 2015

(87) PCT Pub. No.: WO2014/027273
PCT Pub. Date: Feb. 20, 2014

(65) Prior Publication Data
US 2015/0205931 A1  Jul. 23, 2015

Related U.S. Application Data

(60) Provisional application No. 61/683,848, filed on Aug. 16, 2012, provisional application No. 61/714,247, filed on Oct. 16, 2012.

(51) Int. Cl.
*H04W 4/00* (2009.01)
*G06F 19/00* (2011.01)
(Continued)

(52) U.S. Cl.
CPC ........ *G06F 19/3418* (2013.01); *A61B 5/0024* (2013.01); *A61B 5/7282* (2013.01);
(Continued)

(58) Field of Classification Search
None
See application file for complete search history.

(56) References Cited

U.S. PATENT DOCUMENTS 6,416,471 B1 7/2002 Kumar et al.
2007/0244994 A1* 10/2007 Bolan ............... H04L 29/12216
709/220
(Continued)

FOREIGN PATENT DOCUMENTS

| CN | 101389265 A | 3/2009 |
|---|---|---|
| WO | 2012063154 A1 | 5/2012 |
| WO | 2012085762 A2 | 6/2012 |

OTHER PUBLICATIONS

Chen, B., et al. Patient Vital Signs Monitoring using Wireless Body Area Network; 2010; Proc. of IEEE Bioengineering Conference; pp. 1-2.

*Primary Examiner* — Michael J Moore, Jr.

(57) ABSTRACT

A medical system (10) including a remote patient monitoring system (40) and an medical body area network (MBAN) system. The remote patient monitoring system (40) is configured to generate and/or update a patient-specific configuration (60) for the MBAN system (12). The MBAN system (12) is controlled by the patient-specific configuration (60) and includes one or more sensor devices (16, 18) and a hub device (20). The sensor devices (16, 18) are configured to measure physiological parameters of a patient (14). The hub device (20) is configured to at least one of: report the physiological data from the sensor devices (16, 18) to the remote patient monitoring system (40); and locally monitor the physiological data of the sensor devices (16, 18) to generate alarms.

20 Claims, 3 Drawing Sheets

(51) Int. Cl.
*H04L 29/08* (2006.01)
*H04L 12/24* (2006.01)
*A61B 5/00* (2006.01)

(52) U.S. Cl.
CPC .......... *A61B 5/746* (2013.01); *G06F 19/3406* (2013.01); *H04L 41/0672* (2013.01); *H04L 67/125* (2013.01); *A61B 2560/0209* (2013.01); *A61B 2560/0271* (2013.01); *A61B 2560/0276* (2013.01)

(56) References Cited

U.S. PATENT DOCUMENTS

| | | | |
|---|---|---|---|
| 2008/0194925 A1 | 8/2008 | Alsafadi et al. | |
| 2009/0069642 A1 | 3/2009 | Gao et al. | |
| 2009/0253487 A1* | 10/2009 | Gagner | G07F 17/3223 463/20 |
| 2011/0077492 A1 | 3/2011 | Kapu et al. | |
| 2011/0149759 A1 | 6/2011 | Jollota | |
| 2012/0063389 A1* | 3/2012 | Abedi | H04L 45/28 370/328 |
| 2012/0106397 A1* | 5/2012 | Abedi | H04W 74/0875 370/255 |
| 2012/0109238 A1 | 5/2012 | Patel et al. | |
| 2013/0039339 A1* | 2/2013 | Rayavarapu | H04W 76/028 370/331 |
| 2013/0219031 A1* | 8/2013 | Schulz | H04L 41/0672 709/221 |
| 2013/0260740 A1* | 10/2013 | Rayavarapu | H04W 76/046 455/422.1 |

* cited by examiner

FIG. 1

PRIOR ART

FIG. 4 ic patient monitoring
CONNECTED PATIENT MONITORING SYSTEM AND METHOD TO PROVIDE PATIENT-CENTRIC INTELLIGENT MONITORING SERVICES

CROSS REFERENCE TO RELATED APPLICATIONS

This application is a national filing of PCT application Serial No. PCT/IB2013/056401, filed Aug. 5, 2013, published as WO 2014/027273 A1 on Feb. 20, 2014, which claims the benefit of U.S. provisional application Ser. No. 61/683,848 filed Aug. 16, 2012 and U.S. provisional application Ser. No. 61/714,247 filed Oct. 16, 2012, both of which are incorporated herein by reference.

The present application relates generally to medical systems. It finds particular application in conjunction with patient monitoring and will be described with particular reference thereto. However, it is to be understood that it also finds application in other usage scenarios and is not necessarily limited to the aforementioned application.

There is a general trend in the healthcare industry towards ubiquitous patient monitoring. Ubiquitous patient monitoring is continuous and patient centric monitoring during the whole patient care cycle. The patient care cycle of a patient can include patient monitoring in one or more of a general ward, a patient's home, a mobile ambulance, and a high acuity area. Ubiquitous patient monitoring can significantly improve quality of care. For example, patient deterioration can be detected at an early stage and early intervention can effectively prevent severe adverse events from happening. The recent advance of wired and/or wireless communication technologies makes ubiquitous patient monitoring feasible.

Medical body area networks (MBANs) are one of the key enabling technologies for ubiquitous patient monitoring and have drawn lots of attention from both academia and the healthcare industry. An MBAN is a wireless network of sensors around, on, and/or in a patient body used for monitoring the patient's physiological data and deliver care services. The clinical benefits of MBANs include: extension of monitoring into care areas that are currently unmonitored; improved healthcare workflow efficiency, safety and clinical outcome; patient mobility, comfort, and infection control; monitoring flexibility and scalability; and reduced overall monitoring costs. This is not intended to be an exhaustive list of benefits.

Figure 1:
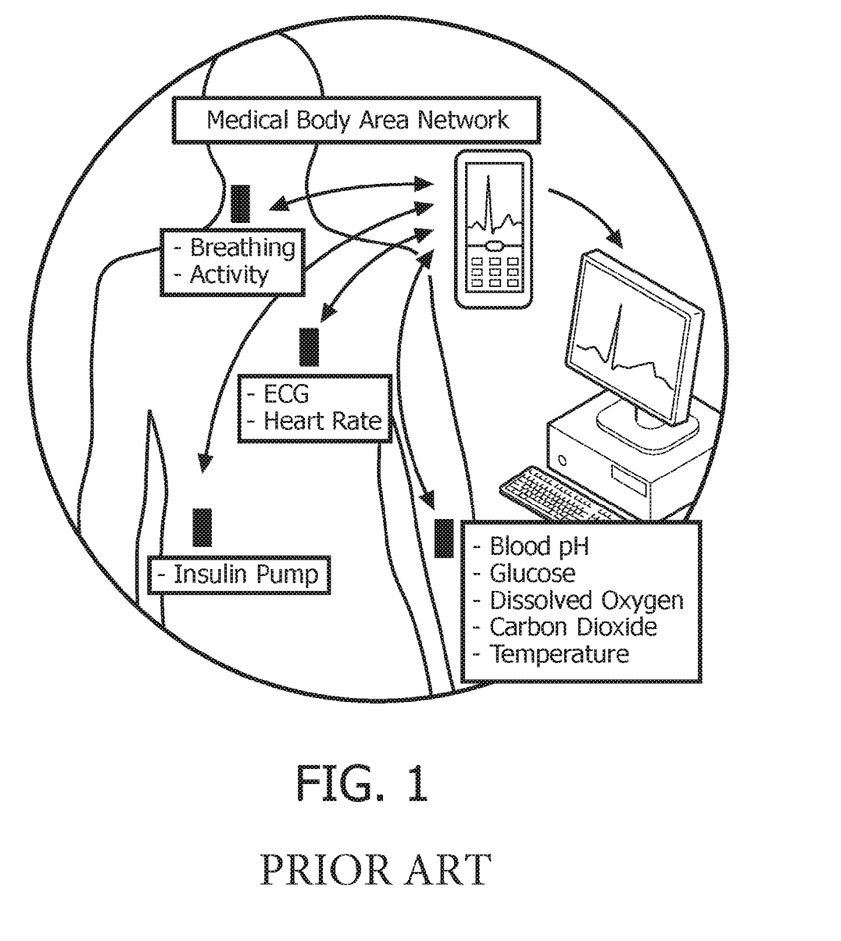
FIG. 1 illustrates a medical body area network (MBAN) system.

With reference to FIG. 1, a typical MBAN system includes several tiny sensor devices placed around, on and/or in a patient's body to capture physiological data of the patient, such as heart rate and electrocardiogram (ECG) data. The captured data is forwarded to a hub device through a short-range and low-power MBAN. The hub device could be a local bedside monitoring unit, a cell phone, a set-top-box, or other wireless device and usually has a connection to a backhaul and/or long-range network (e.g., a third generation or fourth generation cellular network, a local area network (LAN), etc.), through which the collected data is further transferred to a remote patient monitoring system. The remote patient monitoring system is responsible for analyzing patients' physiological data and provides monitoring, diagnosing or treating services in real time.

Such a wireless patient monitoring system allows patients to walk around a medical institution, such as a hospital, and/or around their homes without discontinuing monitoring services. This makes it possible to discharge a patient earlier, but still provide high quality monitoring services at the patient's home, and can reduce healthcare costs. Further, with early warning systems and patient deterioration detection algorithms deployed at the remote patient monitoring system, severe adverse events can be effectively prevented via early intervention and healthcare costs can be reduced. Even more, cheap, portable hub devices can replace expensive dedicated monitors.

Despite the advantageous of MBANs, there are several challenges in designing such systems. One such challenge is connectivity robustness. Since patients can wander around and may even go outside healthcare facilities, the network connectivity between the hub device and the remote patient monitoring system becomes unpredictable and could change significantly. In a worst case, the communication link could be broken. A patient monitoring system should be robust to any network condition changes and always maintain reasonable monitoring performance. This is also critical to meet the federal communications commission (FCC) and food and drug administration (FDA) risk management requirements. Notably, however, in most conventional patient monitoring systems, patients are entangled in the bed and connected with the bedside monitors via cables. Hence, the connectivity issue is less severe there.

Another challenge to MBANs is optimized patient-centric intelligent monitoring setup. Currently one of the big issues faced by current patient monitoring systems is alarm fatigue. Alarm fatigue is the generation of too many false alarms, which can cause caregivers to ignore all alarms, including useful alarms. One of the reasons for alarm fatigue is usually the use of a simple, single-parameter alarming algorithm based on thresholds to generate alarms, where the thresholds used to generate alarms are not customized and updated timely based on a patient's health condition. Instead, some general alarming parameters are used, which may not match patient specific needs well.

An optimized, patient-centric, and intelligent monitoring method is important to ubiquitous patient monitoring since different patients may have different monitoring needs and since even the same patient may have different monitoring needs at different care phases (e.g., at the intensive care unit (ICU), at the recovery area, and at home). A patient monitoring system should provide flexibility to meet diverse monitoring requirements with minimum need of caregiver intervention. Specifically, it should be able to tailor the monitoring solution specifically for a patient based on patient electronic medical record (EMR), medical history profile, current health conditions, and so on. Further, it should be able to automatically configure the monitoring devices with no or minimal intervention of caregivers. This would improve workflow efficiency and quality of care.

Another challenge to MBANs is battery life. In wireless patient monitoring systems, portable hub devices (e.g., portable monitors, tablets, smartphones, etc.) and sensor devices are usually battery powered. A long battery life is desired to reduce the overhead of changing batteries. Also the hub device usually has a limited computing capability and may not be able to support computing extensive alarming and/or signal processing tasks. Hence, it is important to simplify the tasks running on the hub and/or sensor devices as much as possible and activate tasks only when needed.

The present application provides new and improved methods and systems which overcome the above-referenced problems and others.

In accordance with one aspect, a medical system is provided. The medical system includes a remote patient monitoring system configured to generate and/or update a patient-specific configuration for a medical body area network (MBAN) system. The medical system further includes the MBAN system controlled by the patient-specific configuration and including one or more sensor devices and a hub device. The sensor devices are configured to measure physiological parameters of a patient. The hub device is configured to at least one of: report the physiological data from the sensor devices to the remote patient monitoring system; and locally monitor the physiological data of the sensor devices to generate alarms.

In accordance with another aspect, a medical method for a hub device of a medical body area network (MBAN) system is provided. Physiological data is received from one or more sensor devices associated with the MBAN system. The sensor devices are configured to measure physiological parameters of a patient. A patient-specific configuration and/or updates to the patient-specific configuration are received from a remote patient monitoring system. The patient-specific configuration controls operation of the MBAN system. The physiological data from the sensor devices is reported to the remote patient monitoring system or the physiological data of the sensor devices is locally monitored to generate alarms.

In accordance with another aspect, a medical system is provided. The medical system includes a remote patient monitoring system configured to dynamically configure one or more medical body area network (MBAN) systems based on patient-specific data. The patient-specific data includes physiological data. The MBAN systems are each configured to at least one of report patient physiological data to the remote patient monitoring system and locally monitor the patient physiological data to generate alarms.

One advantage resides in improved robustness.

Another advantage resides in optimized patient-centric monitoring.

Another advantage resides in improved battery life.

Another advantage resides in minimal caregiver intervention.

Another advantage resides in improved configuration.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 2:
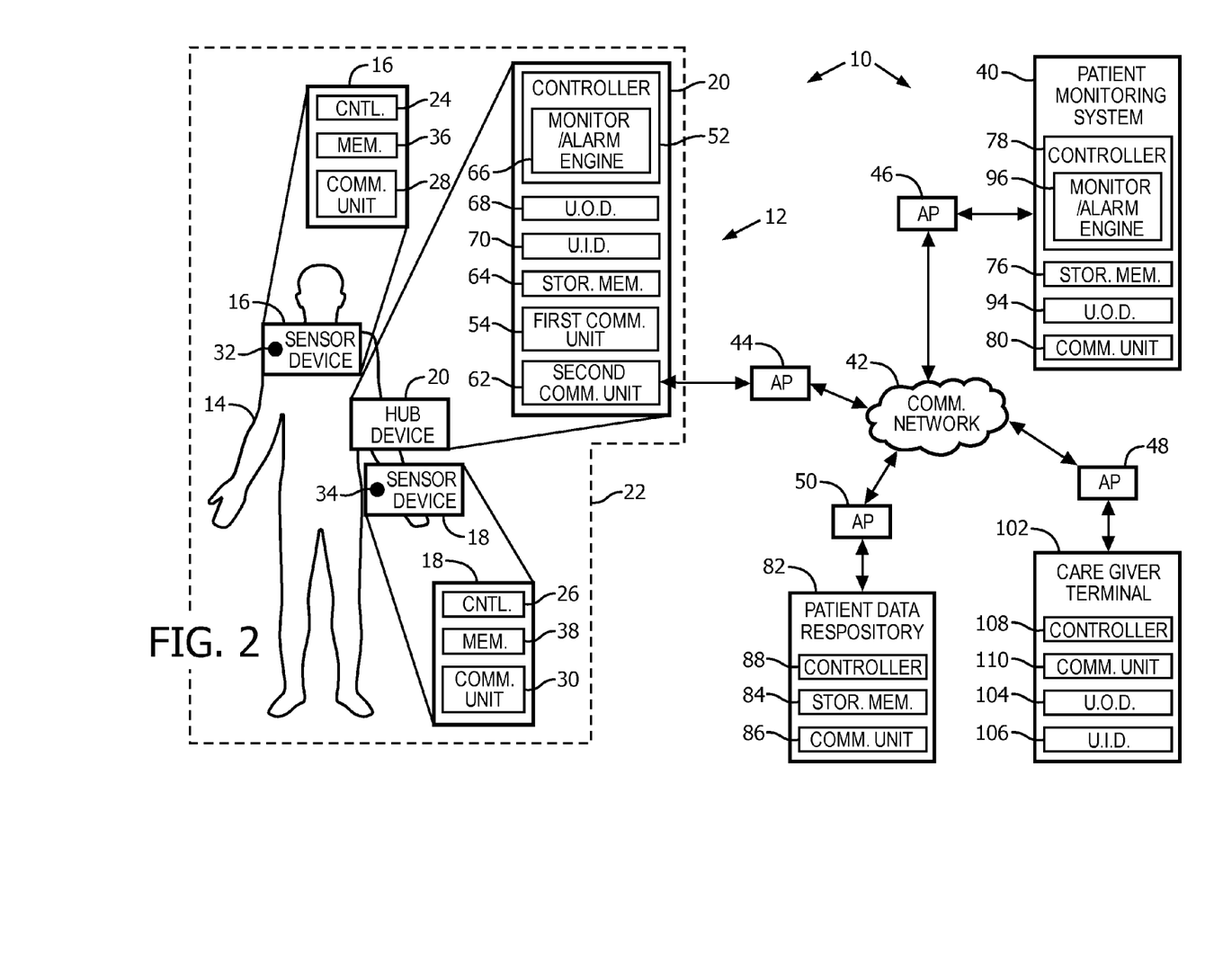
FIG. 2 illustrates a block diagram of a medical system.

With reference to FIG. 2, a medical system 10 includes one or more medical body area network (MBAN) systems 12. The MBAN systems 12 are each associated with a patient 14 and are each deployed to capture physiological data of the patient 14. Further, each of the MBAN systems 12 includes one or more sensor devices 16, 18 and a hub device 20 communicating over an MBAN 22 of the MBAN system 12. The MBAN 22 is a low-power, short-range wireless network, such as IEEE 802.15.6 or IEEE 802.15.4j wireless network.

The sensor devices 16, 18 capture physiological data of the patient 14, such as heart rate, respiration rate, blood pressure, ECG signals, and so forth, in real-time and forward the data to the hub device 20 over the MBAN 22. The sensor devices 16, 18 are typically disposed on the exterior of the patient 14. For example, the sensor devices 16, 18 can be on-body and/or wearable sensor devices. However, in some embodiments, the sensor devices 16, 18 are additionally or alternatively disposed in the patient 14 and/or proximate to the patient 14.

Each of the sensor devices 16, 18 includes a controller 24, 26, a communication unit 28, 30, and at least one sensor 32, 34 for measuring at least one physiological parameter of the patient 14. The controller 24, 26 captures the physiological data using the at least one sensor 32, 34 and transmits the captured physiological data to the hub device 20 using the communication unit 28, 30. The controller 24, 26 can immediately transmit the captured physiological data upon receiving it. Alternatively, the controller 24, 26 can buffer or otherwise store the captured physiological data in a storage memory 36, 38 of the sensor device 16, 18 and only transmit the buffered physiological data when the amount exceeds a threshold. The communication unit 28, 30 communicates with the hub device 20 over the MBAN 22.

Typically, the captured physiological data is transmitted directly to the hub device 20 using the communication unit 28, 30. However, the captured physiological data can be indirectly transmitted to the hub device 20. For example, the sensor devices 16, 18 can transmit the physiological data to a patient-carried unit with, for example, body coupled communications. The patient-carried unit can then transmit the physiological data from all of the sensor devices 16, 18 to the hub device 20.

The hub device 20 one or more of: 1) collects physiological data from the sensor devices 16, 18; 2) manages the sensor devices 16, 18 (e.g., acts as a personal area network (PAN) coordinator); 3) processes collected physiological data locally, typically in real-time; 4) facilitates remote configuration of the MBAN system 20; and 5) transfers collected physiological data to a patient monitoring system 40 of the medical system 10 over a second communication network 42, such as a wired Ethernet, Wi-Fi, or 3G/4G cellular network. The second communication network 42 is typically long-range compared to the MBAN 22. When the second communication network 42 includes a wireless interface, it includes one or more access points 44, 46, 48, 50 for wireless communication. The hub device 20 is typically disposed proximate to the patient 14. Further, the hub device 20 is typically one of a local bedside monitoring unit, a cell phone, a set-top-box, or other wireless device.

Figure 3:
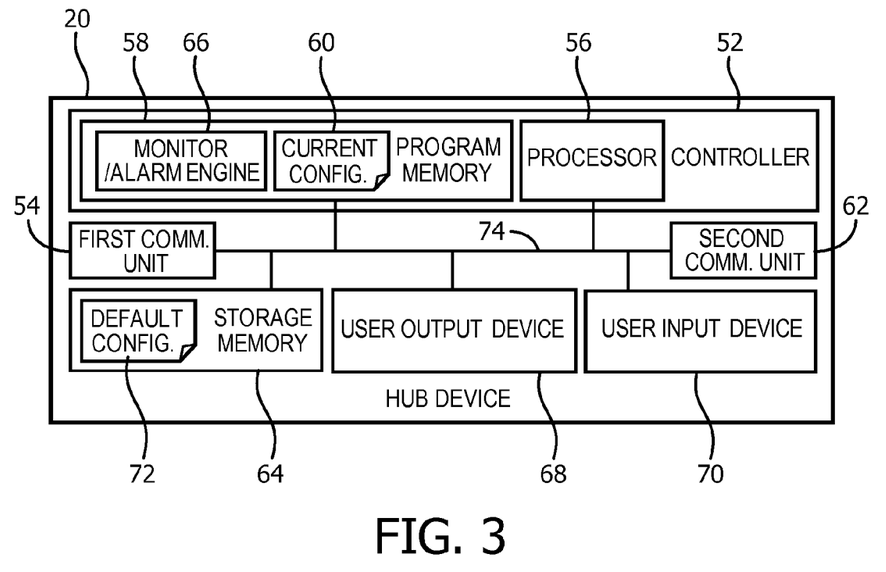
FIG. 3 illustrates a block diagram of a hub device.

With continuing reference to FIG. 2, and further reference to FIG. 3, the hub device 20 includes a controller 52 and a first communication unit 54. The first communication unit 54 communicates with the sensor devices 16, 18 using the MBAN 22. The controller 52 can communicate with the MBAN 22 using the first communication unit 54. The controller 52 includes at least one processor 56 and at least one program memory 58. The program memory 58 includes processor executable instructions executed by the processor 56 to perform the below described functions of the controller 52. The program memory further includes a current configuration 60 for the MBAN system 12.

The controller 52 can act as the PAN coordinator for the MBAN 22 using the first communication unit 54. In doing so, the controller 52 controls the first communication unit 54 to set up the MBAN 22, associate/disassociate the sensor device 16, 18 with the MBAN 22, and so on. The controller 52 can further receive the captured physiological data from the sensor devices 16, 18 using the first communication unit 54.

The controller 52 can also transmit the received physiological data to the patient monitoring system 40 using a second communication unit 62 of the hub device 20. The controller 52 can immediately transmit the received physiological data to the patient monitoring system 40 upon receiving it. Alternatively, the controller 52 can buffer or otherwise store the received physiological data in a storage memory 64 of the hub device 20 and only transmit the buffered physiological data when the amount exceeds a threshold. The second communication unit 62 communicates with the patient monitoring system 40 using the second communication network 42.

The controller 52 further includes a monitor and/or alarm engine 66 to generate real-time local alarms. The monitor and/or alarm engine 66 is a software module of processor executable instructions stored on the program memory 58 and executed by the processor 56.

The monitor and/or alarm engine 66 includes one or more alarm generation algorithms, each typically tailored to different operating states (e.g., power modes or type of hub device, such as bedside monitor or mobile hub device) of the MBAN system 12, and processes the collected physiological data locally using at least one of the alarm generation algorithms. In response to detecting an alarm condition, the monitor and/or alarm engine 66 can generate warning messages, such as audio and/or visual warning messages using, for example, a user output device 68 (e.g., a display device) of the hub device 20. Additionally, or alternatively, the monitor and/or alarm engine 66 can transmit an alarm message to the patient monitoring system 40 over the second communication network 42 so as to allow the patient monitoring system 40 to process the alarm and alert caregivers.

The controller 52 can also report the operating state of the MBAN system 12. For example, the controller 52 can report one or more of a patient identifier (ID), the capabilities of the hub device 20 (e.g., whether the hub device 20 is battery or alternating current (AC) powered and data regarding one or more of a central processing unit (CPU), a memory, a display, a network, etc. of the hub device 20), and associated sensor device capability data (e.g., type of sensors) of the hub device 20 to the patient monitoring system 40. Typically, the reporting is performed once an MBAN system 12 is prescribed by a doctor, deployed on a patient, and activated.

The controller 52 can further allow the MBAN system 12 to be remotely configured by, for example, the patient monitoring system 40 through the second communication network 42. Additionally or alternatively, the controller 52 can allow the MBAN system 12 to be locally configured. For example, the hub device 20 can receive input from the user with a user input device 70 (e.g., touch screen, buttons, etc.) of the hub device 20 to locally configure the hub device 20.

The current configuration 60 can include a configuration for the monitor and/or alarm engine 66. The configuration for the monitor and/or alarm engine 66 can include one or more of: 1) a selection of one of the alarm generation algorithms for use; 2) thresholds and/or parameters used by the selected alarm generation algorithm; 3) medical rules used by the selected alarm generation algorithm; 4) an enable/disable flag for the monitor and/or alarm engine 66; 5) and so on. For example, simple rule based alarm algorithms may be suitable for some well studied diseases on battery-powered hub devices, while complicated data-driven machine learning alarm algorithms may be suitable for hub devices (e.g., set-top boxes, bedside monitors, and so on) powered by a power grid (e.g., an alternating current (AC) power grid) on some specific diseases.

The current configuration 60 can further include a configuration for the sensor devices 16, 18. The configuration for the sensor devices 16, 18 can include one or more of: 1) the types of physiological data to be monitored; 2) the sampling rates and/or precision for the monitored types of physiological data; 3) the types of sensor devices to be enabled and/or activated; 4) parameters of the enabled and/or activated sensor devices, such as sampling rates and analog to digital convert (ADC) bit-width; 5) and so on.

The current configuration 60 can further include a configuration for reporting by the controller 52 to the patient monitoring system 40. The configuration for reporting to the patient monitoring system 40 can include one or more of: 1) the types of physiological data to be reported to the patient monitoring system 40, such as raw physiological data, down-sampled physiological data, pre-processed physiological data, or the like; 2) the reporting rates for the different types of physiological data; and 3) and so on.

The controller 52 can further dynamically switch between different configurations depending upon the operating state of the MBAN system 12 (e.g., power modes, connectivity, type of hub device, etc.). For example, the controller 52 can continuously monitor the quality of the network connection with the patient monitoring system 40. Once an outage of the network connection with the patient monitoring system 40 is detected, it automatically switches to a default configuration 72 saved locally in a the storage memory 64 of the hub device 20 to reconfigure the monitor and/or alarm engine 66 and enable the monitor and/or alarm engine 66 to provide local alarming services. The controller 52 can also generate warning messages in response to changing the configuration. For example, a warning message can be generated for the network outage, such as audio and/or visual warning messages using, for example, the user output device 68.

At least one system bus and/or communication network 74 interconnect components of the hub device 20, including the controller 52 (i.e., the program memory 58 and the processor 56), the storage memory 64, the user output device 68, the user input device 70, the first communication device 54, and the second communication device 62. Further, although the components of the hub device, other than the processor 56 and the program memory 58, are illustrated as external to the controller 52, one or more of these components can be integrated with the controller 52.

Referring back to FIG. 2, the patient monitoring system 40 one or more of: 1) receives physiological data forwarded by the hub devices 20 over the second communication network 42; 2) analyzes the received physiological data; 3) stores the received physiological data in a storage memory 76 of the patient monitoring system 40 or in an external system; 4) provides monitoring, diagnosing or treating services in real time based on the received physiological data; and 5) so on. The patient monitoring system 40 is typically remote from the MBAN systems 12.

Figure 4:
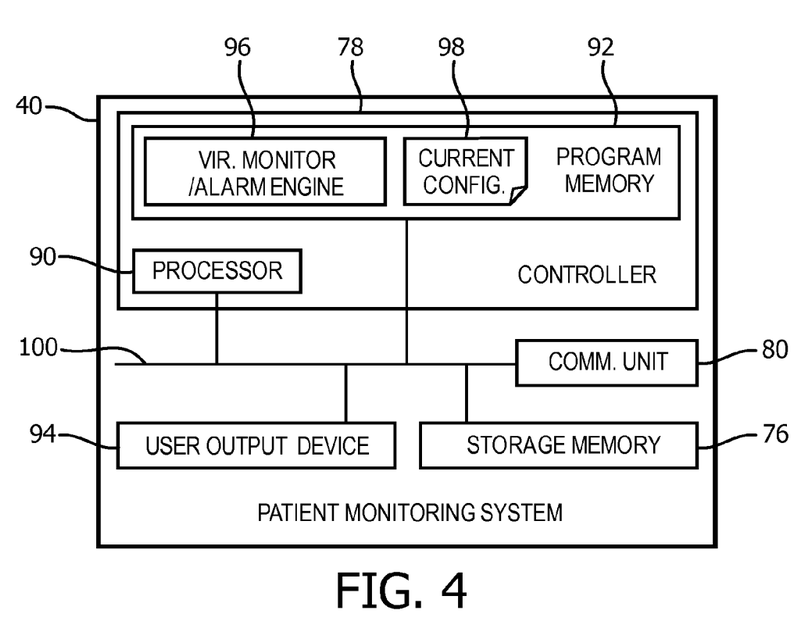
FIG. 4 illustrates a block diagram of a patient monitoring system.

With continuing reference to FIG. 2, and further reference to FIG. 4, the patient monitoring system 40 includes a controller 78 and a communication unit 80. The communication unit 80 allows the controller 78 to communicate with devices or systems over the second communication network 42. For example, the communication unit 80 allows the controller 78 to communicate with the MBAN systems 12, specifically the hub devices 20 of the MBAN systems 12, over the second communication network 42. As another example, the communication unit 80 allows the controller 78 to communicate with a patient data repository 82 of the medical system 10.

The patient data repository 82 stores patient medical data profiles for the patients 14 of the MBAN systems 12 in one or more storage memories 84 of the patient data repository 82. Such profiles may include electronic medical records (EMRs), medical history data, lab reports, physiological data, doctor prescription about the configuration of the MBAN system (e.g., which physiological data should be monitored), and other relevant patient data. The patient data repository 82 may also store other medical data that may be useful for clinical decision support algorithms, such as medical knowledge, demographic and/or geographic medical data, and so on in the storage memories 84.

The patient data repository 82 further includes a communication unit 86 and a controller 88. The communication unit 86 allows the controller 88 to communicate with the second communication network 42, and the controller 88 makes the data in the memories 84 available over the second communication network 42. The controller 78 of the patient monitoring system 40 includes at least one processor 90 and at least one program memory 92. The program memory includes processor executable instructions executed by the processor to perform the below described functions of the controller 78.

The controller 78 can receive physiological data from each of the hub devices 20. The controller 78 can also monitor and/or track patient health conditions (as determined from the physiological data) and issue alarms based thereon. The controller 78 can determine whether to issue an alarm by matching the received physiological data to alarm criteria. For example, an alarm can be issued if at least one physiological parameter exceeds a threshold. The alarm criteria can take in to account the present values of physiological parameters, as well as trends of physiological parameters. The controller 78 can also generate early warnings based on long-term patient health condition prediction. Further, the controller 78 can present (e.g., display) the received physiological data on a user output device 94 of the patient monitoring system 40 and/or store the received physiological data in the storage memory 76 of the patient monitoring system 40 or the patient data repository 82. The controller 78 can also generate and/or adjust patient specific monitoring configurations for each MBAN system 12.

The controller 78 can also receive data regarding the operating states of the MBAN systems 12, typically as the MBAN systems 12 are prescribed, deployed and activated. For each of the MBAN systems 12, the controller 78 can use the corresponding data, such as patient ID, to retrieve the doctor prescription about the configuration of the MBAN system 12 (e.g., which physiological data should be monitored) from, for example, the patient data repository 72, and check if the prescribed sensor devices 16, 18 are correctly deployed. This can avoid mistakes made by caregivers in configuring the MBAN system 12.

The controller 78 can also use the corresponding data to retrieve a patient medical data profile for the patient from the patient data repository 82. Based on the data in the patient medical data profile, such as patient conditions, and the corresponding data, such as the capabilities of the hub device 20, the controller 78 can generate a recommended configuration for the MBAN system 12 specifically tailored to the patient 14. The controller 78 can compare the recommended configuration with the prescribed configuration. If there is a big difference, the controller 78 can generate warning messages to report the identified difference to caregivers, such as doctors and nurses. Further, the controller 78 can use the recommended configuration to setup the MBAN system 12 via the second communication network 42 and start monitoring services, typically if there are no big differences.

The controller 78 can also generate default configurations 72 for the MBAN systems 12, which the hub devices 20 will save locally. The hub devices 20 can employ the default configurations 72 depending upon the operating states of the MBAN systems 12. For example, the default configuration 72 of an MBAN system 12 can be employed if the hub device 20 loses connectivity with the patient monitoring system 40.

The default configurations 72 can be different from the current configurations 60 used by the MBAN systems 12 and usually are more conservative to provide sufficient local monitoring services. For example, the default configuration 72 of an MBAN system 72 can be more conservative compared to the configuration used when the MBAN system 12 is connected with the patient monitoring system 40 by way of the hub device 20. When the MBAN system 12 is connected with the patient monitoring system 40, more physiological data can be monitored and analyzed at the patient monitoring system 40. Further, when the MBAN system 12 is not connected with the patient monitoring system 40, more conservative alarming thresholds can be employed to ensure reasonable monitoring performance.

The controller 78 can dynamically update the current and/or default configurations 60, 72 of the MBAN systems 12 based on patient condition changes. During the monitoring process, the controller 78 can continuously monitor patient health conditions based on the latest physiological data of the patients 14 and adjust the current and/or default configurations 60, 72 accordingly. The adjustments can be performed using, for example, a machine learning and/or data mining algorithm to evaluate and/or predict a patient health condition with the patient medical data profiles and/or the real-time physiological data.

For example, if patient deterioration is detected, the controller 78 can reconfigure the MBAN system 12 to activate more sensor devices 16, 18 (e.g., wake up wearable sensors which are in a sleep mode) to monitor more physiological data. Alternatively, the controller 78 can increase the sampling rate and/or precision of activated sensor devices 16, 18 to get more precise patient physiological data. As another example, if a patient in a step-down area recovers well and patient health conditions becomes stable, the controller 78 can deactivate some sensor devices 16, 18 (e.g., put wearable sensors into sleep mode) to stop monitoring unnecessary physiological data.

The controller 78 can also continuously monitor the operating states of the MBAN systems 12 (e.g., power modes, connectivity, etc.), such as the quality of the network connections with the hub devices 20. Based thereon, alarms can be generated and/or the current and/or default configurations 60, 72 can be updated. For example, in response to detecting a degradation in the quality of a network connection, the controller 78 can update the current and/or default configurations of the MBAN system 12 accordingly and/or generate warning messages to healthcare staff.

As another example, if the network connection with a hub device 20 is in a good condition (e.g., in terms of throughput and latency), the controller 78 can disable the monitoring/alarm engine 66 on the hub device 20 and perform real-time alarming algorithms by itself. The generated alarms can then be sent back to the hub device 20 to generate alarm messages and/or signals at the point of care. Such a setup would minimize the data processing at the hub device 20 and prolong the battery life of the hub device 20.

As another example, if network congestion of the second communication network 42 is detected for an MBAN system 12, the controller 78 can enable the monitoring/alarm engine 66 of the MBAN system 12 to run a simple real-time threshold based alarming algorithm on the hub device 20.

Network congestion can be detected when the throughput and latency become worse due to, for example, the patient 14 going to an operating room (OR) waiting area where many patients are co-located with MBANs 22 operating on them.

The controller 78 can also use data-driven algorithms to continuously optimize the thresholds used by the monitoring/alarm engine 66 of the hub device 20. The simple local alarming algorithm would allow the hub device 20 to detect any real-time abnormal conditions. The thresholds continuously optimized by the controller 78 can help avoid generating too many false alarms.

Further, if network congestion of the second communication network 42 is detected, the controller 78 can request the hub device 20 to down-sample the captured physiological data and send down-sampled data to the patient monitoring system 40. For example, the sensor devices 16, 18 can measure blood pressure once every two minutes, but the hub device 20 can report one measurement to the patient monitoring system 40 every 10 minutes. By doing so, the traffic between the patient monitoring system 40 and the hub devices 20 is reduced to mitigate network congestion.

As another example, if patient deterioration is detected and the patient 14 is transported from the general ward to the intensive care unit (ICU), the hub device 20 can be switched from a portable monitor to a bedside monitor, which has a much more powerful CPU and is AC powered. The controller 78 can use a more complicated local alarming algorithm on the bedside monitor to generate more local real-time alarms. Similarly, during transportation, the hub device 20 could be switched from a bedside monitor to a portable monitor with less computing capability. The controller 78 can use a simpler local alarming algorithm for the new hub device 20 and perform some complicated signal processing tasks at the patient monitoring system 40.

The controller 78 can include a virtual monitor and/or alarm engine 96 to generate real-time local alarms in accordance with configurations 98 specified by caregivers. The virtual monitor and/or alarm engine 96 allows caregivers to establish individual monitor and/or alarm engines. Additionally or alternatively, the virtual monitor and/or alarm engine 96 allows caregivers to try different configurations before they are applied to the monitor and/or alarm engines 66 of the hub devices 20. The virtual monitor and/or alarm engine 96 is a software module of processor executable instructions stored on the program memory 92 and executed by the processor 90.

At least one system bus and/or communication network 100 interconnect components of the patient monitoring system 40, including the controller 78 (i.e., the program memory 92 and the processor 90), the storage memory 76, the user output device 94, and the communication device 80. Further, although the components of the patient monitoring system 40, other than the processor 90 and the program memory 92, are illustrated as external to the controller 76, one or more of these components can be integrated with the controller 76.

One or more caregiver terminals 102 allow caregivers to interface with other devices of the second communication network 42, such as the patient monitoring system 40 and/or the patient data repository 82. Caregivers can use the caregiver terminals 102 to connect (e.g., login) to the patient monitoring system 40 and/or the patient data repository 82 and access patient data.

Moreover, the caregivers can use the caregiver terminals 102 to each connect to the patient monitoring system 40 and/or the patient data repository 82 and establish and/or modify configurations for the monitor/alarm engines 66 of the hub devices 20 and/or the virtual monitor/alarm engine 96 of the patient monitoring system 40. Caregivers can customize their configurations based on their preferences. Further, caregivers can access their configurations from any one of the caregiver terminals 102. The configurations can be indexed based on, for example, caregiver ID or patient ID.

Even more, caregivers can use the caregiver terminals 102 to run their configurations with the virtual monitor and/or alarm engine 96 of the patient monitoring system 40. The virtual monitor and/or alarm engine 96 generates alarms based on the rules and/or algorithms specified by select configurations and send alarms back to the caregivers over the second communication network 42. For example, a caregiver can select one of their configurations to run in the virtual monitor and/or alarm engine 96. The virtual monitor and/or alarm engine 96 will then forward generated alarms to the caregiver at the terminal 102 of the caregiver.

Further, the caregiver can use the caregiver terminals 102 to receive physiological data and/or alarms from the patient monitoring system 40. User output devices 104 of the caregiver terminals 102 can present (e.g., display) the physiological data and/or alarms to the caregivers. Further, user input devices 106 of the caregiver terminals 102 can allow the caregivers to interact with the presented physiological data and/or alarms.

The caregiver terminals 102 each include a controller 108 and a communication unit 110. The communication unit 110 allows the controller 108 to communicate with devices over the second communication network 42. The controller 108 includes at least one processor and at least one program memory. The program memory includes processor executable instructions executed by the processor to perform the above described functions of the controller. The caregiver terminals 102 can also each include a user input device 106 and a user output device 104. The user input device 106 allows a caregiver to input data to the controller 108, and a user output device 104 allows the controller 108 to convey data to the caregiver. Examples of the caregiver terminals include personal computers (PCs), tablets, smartphones, and so on.

The above described scheme can be used in patient monitoring and/or clinical decision support systems, such as eICU, bedside monitors, and home monitoring solutions. Advantageously, the scheme improves patient monitoring robustness, provides optimized patient-centric monitoring, and improves battery life of the devices of the MBAN systems.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a controller includes: 1) at least one memory with processor executable instructions to perform the functionality of the controller; and 2) at least one processor executing the processor executable instructions; a user output device includes a printer, a display device, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A medical system comprising:
a remote patient monitoring system configured to generate and/or update a patient-specific configuration for a medical body area network (MBAN) system in response to a change in the patient condition; and,
the MBAN system controlled by the patient-specific configuration and including one or more sensor devices and a hub device, the sensor devices configured to measure physiological parameters of a patient, and the hub device includes a default configuration received from the remote patient monitoring system and is configured to:
monitor for a loss of network connectivity between the hub device and the remote patient monitoring system wherein the current configuration of the MBAN system is replaced with the default configuration in response to the loss of network connectivity; and
at least one of:
report the physiological data from the sensor devices to the remote patient monitoring system; and,
locally monitor the physiological data of the sensor devices to generate alarms.

2. The medical system according to claim 1, wherein the patient-specific configuration includes at least one of a configuration for locally monitoring the physiological data, a configuration for the sensor devices, and a configuration for reporting the physiological data to the remote patient monitoring system.

3. The medical system according to claim 1, wherein the remote patient monitoring system is configured to update at least one of the patient-specific configuration and the default configuration based on at least one of patient-specific data, the physiological data, and an operating state of the MBAN system.

4. The medical system according to claim 1, wherein the remote patient monitoring system is configured to update at least one of the patient-specific configuration and the default configuration in response to a change in an operating state of the MBAN system, the operating state of the MBAN system including one or more of power mode of the hub device, connectivity of the hub device the patient monitoring system, capabilities of the hub device, and capabilities of the sensor devices.

5. The medical system according to claim 1, wherein the remote patient monitoring system is configured to update at least one of the patient-specific configuration and the default configuration in response to a change in the patient condition.

6. The medical system according to claim 1, wherein the remote patient monitoring system is configured to update at least one of the patient-specific configuration and the default configuration in response to congestion on a network through which the MBAN system and the remote patient monitoring system communicate.

7. The medical system according to claim 1, wherein the remote patient monitoring system is configured to:
compare the patient-specific configuration to a patient-specific configuration prescribed by a caregiver of the patient, and,
generate an alert if a difference between the patient-specific configuration and the prescribed patient-specific configuration exceeds a threshold.

8. The medical system according to claim 1, wherein the default configuration enables local monitoring of the physiological data on the hub device.

9. The medical system according to claim 1, wherein the remote patient monitoring system includes a virtual monitor and/or alarm engine, the virtual monitor and/or alarm engine being configured to monitor the physiological data in accordance with configurations generated by caregivers.

10. A medical method for a hub device of a medical body area network (MBAN) system, said method comprising:
receiving physiological data from one or more sensor devices associated with the MBAN system, the sensor devices configured to measure physiological parameters of a patient;
receiving a patient-specific configuration from a remote patient monitoring system, wherein the patient-specific configuration controls operation of the MBAN system;
receiving a default configuration from the remote patient monitoring system;
monitoring for a loss of network connectivity between the hub device and the remote patient monitoring system wherein the current configuration of the MBAN system is replaced with the default configuration in response to the loss of network connectivity; and
at least one of:
reporting the physiological data from the sensor devices to the remote patient monitoring system; and,
locally monitoring the physiological data of the sensor devices to generate alarms.

11. The medical method according to claim 10, wherein the patient-specific configuration includes at least one of a configuration for locally monitoring the physiological data, a configuration for the sensor devices, and a configuration for reporting the physiological data to the remote patient monitoring system.

12. The medical method according to claim 10, wherein at least one of the patient-specific configuration and the default configuration is based on at least one of patient-specific data, the physiological data, and an operating state of the MBAN system.

13. The medical method according to claim 10, further including:
receiving an update to at least one of the patient-specific configuration and the default configuration in response to a change in an operating state of the MBAN system, the operating state of the MBAN system including one or more of power mode of the hub device, connectivity of the hub device to the remote patient monitoring system, capabilities of the hub device, and capabilities of the sensor devices.

14. The medical method according to claim 10, further including:
receiving an update to at least one of the patient-specific configuration and the default configuration in response to a change in the patient condition.

15. The medical method according to claim 10, further including:
receiving an update to at least one of the patient-specific configuration and the default configuration in response to congestion on a network through which MBAN system and the remote patient monitoring system communicate.

16. The medical method according to claim 10, wherein the default configuration enables local monitoring of the physiological data on the hub device.

17. A hub device comprising:
at least one interface;
a memory configured to store a patient-specific configuration and a default configuration; and
a processor in communication with the interface and the memory, wherein the processor is configured to:
receive physiological data from one or more sensor devices via the at least one interface,
receive a patient-specific configuration from a remote patient monitoring system via the at least one interface, wherein the received patient-specific configuration is stored in the memory;
receive a default configuration from the remote patient monitoring system via the at least one interface wherein the received default configuration is stored in the memory;
monitor for a loss of network connectivity at the at least one interface to the remote patient monitoring system wherein a current configuration is replaced with the default configuration in response to the loss of network connectivity; and
at least one of:
reporting the physiological data from the sensor devices to the remote patient monitoring system; and,
locally monitoring the physiological data of the sensor devices to generate alarms.

18. The hub device of claim 17, wherein, in replacing the current configuration with the default configuration, the processor is configured to alter a configuration of the one or more sensor devices.

19. The hub device of claim 18 wherein, in altering the configuration of the one or more sensor devices, the processor is configured to change the activation status of at least one of the sensor devices.

20. The hub device of claim 17, wherein the replacement of the current configuration with the default configuration causes the processor to begin locally monitoring the physiological data to generate alarms.

* * * * *